US00PP17861P2

(12) United States Plant Patent
Bergman

(10) Patent No.: US PP17,861 P2
(45) Date of Patent: Jul. 10, 2007

(54) ***CHRYSANTHEMUM* PLANT NAMED 'YOORCHARD LAKE'**

(50) Latin Name: *Chrysanthemum×morifolium*
Varietal Denomination: Yoorchard Lake

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 8 days.

(21) Appl. No.: 11/269,177

(22) Filed: Nov. 8, 2005

(51) Int. Cl.
*A01H 5/00* (2006.01)

(52) U.S. Cl. ..... Plt./288
(58) Field of Classification Search ..... Plt./288
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Yoorchard Lake', characterized by its upright and mounded plant habit; vigorous and strong growth habit; large dark green-colored foliage; uniform flowering response and habit; early flowering habit; large decorative incurved-type inflorescences with elongated oblong-shaped and white-colored ray florets with purple-colored apices; and good postproduction longevity with plants maintaining good substance and color for about three to four weeks in an interior environment.

2 Drawing Sheets

Botanical designation: *Chrysanthemum×morifolium.*
Cultivar denomination: 'Yoorchard Lake'.

BACKGROUND OF THE INVENTION

The present Invention relates to a new and distinct cultivar of *Chrysanthemum* plant, botanically known as *Chrysanthemum×morifolium* and hereinafter referred to by the name 'Yoorchard Lake'.

The new *Chrysanthemum* is a product of a planned breeding program conducted by the Inventor in Salinas, Calif. and Alva, Fla. The objective of the program is to create or discover new potted *Chrysanthemum* cultivars that are suitable for year-round production with uniform plant growth habit, good vigor, desirable inflorescence form and floret colors, fast and uniform flowering response and good postproduction longevity.

The new *Chrysanthemum* originated from a cross-pollination made in February, 2000 in Salinas, Calif., of a proprietary selection of *Chrysanthemum×morifolium* identified as code number YB-A0358, not patented, as the female, or seed, parent with a proprietary selection of *Chrysanthemum×morifolium* identified as code number YB-4640, not patented, as the male, or pollen, parent. The new *Chrysanthemum* was discovered and selected by the Inventor as a single flowering plant within the progeny of the stated cross-pollination grown in a controlled environment in Alva, Fla., in November, 2000. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in March, 2001. Asexual reproduction by cuttings has shown that the unique features of this new *Chrysanthemum* are stable and reproduced true to type in successive generations.

SUMMARY OF THE INVENTION

The cultivar Yoorchard Lake has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoorchard Lake'. These characteristics in combination distinguish 'Yoorchard Lake' as a new and distinct *Chrysanthemum:*

1. Upright and mounded plant habit.
2. Vigorous and strong growth habit.
3. Large dark green-colored foliage.
4. Uniform flowering response and habit.
5. Typically grown as a single stem (nonpinched) disbud-type.
6. Early flowering habit.
7. Large decorative incurved-type inflorescences with elongated oblong-shaped ray florets.
8. White-colored ray florets with purple-colored apices.
9. Good postproduction longevity with plants maintaining good substance and color for about three or four weeks in an interior environment.

Plants of the new *Chrysanthemum* can be compared to plants of the female parent selection. Plants of the new *Chrysanthemum* differ from plants of the female parent selection in the following characteristics:

1. Plants of the new *Chrysanthemum* have larger inflorescences than plants of the female parent selection.
2. Plants of the new *Chrysanthemum* and the female parent selection differ in ray floret color as plants of the female parent selection have pink and dark pink bi-colored ray florets.

Plants of the new *Chrysanthemum* can be compared to plants of the male parent selection. Plants of the new *Chrysanthemum* differ from plants of the male parent selection in the following characteristics:

1. Plants of the new *Chrysanthemum* are more vigorous than plants of the male parent selection.
2. Plants of the new *Chrysanthemum* and the male parent selection differ in ray floret coloration as plants of the male parent selection have solid white-colored ray florets.
3. Inflorescences of plants of the new *Chrysanthemum* produce few disc florets whereas inflorescences of plants of the male parent selection produce many disc florets.

Plants of the new *Chrysanthemum* can be compared to plants of the cultivar Chalurido (U.S. Plant Pat. No. 9,502) also known as 'Violet Cymbal'. In side-by-side comparisons conducted in Alva. Fla., plants of the new *Chrysanthemum* differed from plants of the cultivar Violet Cymbal in the following characteristics:

1. Plants of the new *Chrysanthemum* were more vigorous than plants of the cultivar Violet Cymbal.
2. Plants of the new *Chrysanthemum* flowered about one week earlier than plants of the cultivar Violet Cymbal.
3. Plants of the new *Chrysanthemum* and the cultivar Violet Cymbal differed in ray floret color as plants of the cultivar Violet Cymbal had purple-colored ray florets.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum*.

The photograph on the first sheet comprises a side perspective view of typical flowering plants of 'Yoorchard Lake' grown as single stem disbud-types.

The photograph on the second sheet comprises a close-up view of a typical inflorescence of 'Yoorchard Lake'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Salinas, Calif., in a fiberglass-covered greenhouse and under conditions which approximate those generally used in commercial potted *Chrysanthemum* production. During the production of these plants, the following conditions were measured: day temperatures, 21° C. to 27° C.; night temperatures, 17° C. to 19° C.; and light levels, 5,000 to 6,000 foot-candles. Four unrooted cuttings were directly stuck in 15-cm containers, exposed to long day/short night conditions, and were grown as single stem (nonpinched) plants. About two weeks later, the photoinductive short day/long night treatments were initiated. Plants used for the description were grown as disbud-types. Measurements and numerical values represent averages of typical flowering plants.

Botanical classification: *Chrysanthemum×morifolium* cultivar Yoorchard Lake.

Commercial classification: Decorative incurved-type potted *Chrysanthemum*.

Parentage:

*Female, or seed, parent.*—Proprietary selection of *Chrysanthemum×morifolium* identified as code number YB-A0358, not patented.

*Male, or pollen, parent.*—Proprietary selection of *Chrysanthemum×morifolium* identified as code number YB-4640, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous decorative incurved-type potted *Chrysanthemum* that is typically grown as a single stem (nonpinched) disbud-type. Upright and columnar; mounded crown. Vigorous and strong growth habit.

*Plant height.*—About 35.5 cm.

*Plant width.*—About 35 cm.

*Lateral branches* (*peduncles*).—Length: About 32 cm. Diameter: About 6 mm. Internode length: About 1.3 cm. Strength: Strong. Texture: Pubescent. Color: 146A.

*Foliage description.*—Arrangement: Alternate; simple. Length: About 11.25 cm. Width: About 7.75 cm. Apex: Cuspidate. Base: Truncate with attenuate tendencies. Margin: Palmately lobed, sinuses between lateral lobes mostly divergent. Texture, upper and lower surfaces: Pubescent. Color: Developing and fully expanded foliage, upper surface: Darker green than 147A. Developing and fully expanded foliage, lower surface: Close to 147B. Venation, upper and lower surfaces: Close to 147B. Petiole length: About 1.8 cm. Petiole diameter: About 3.5 mm. Petiole texture, upper and lower surfaces: Pubescent. Petiole color, upper surface: Close to 146A. Petiole color, lower surface: Close to 146B.

Inflorescence description:

*Appearance.*—Decorative incurved-type inflorescence form with elongated oblong-shaped ray florets. Inflorescences borne on terminals above foliage. Disk and ray florets develop acropetally on a capitulum. Inflorescences slightly fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to three weeks of long day/short night conditions followed by photoinductive short day/long night conditions flower about eight weeks later.

*Postproduction longevity.*—Inflorescences maintain good color and substance for about three to four weeks in an interior environment.

*Quantity of inflorescences.*—Grown as a disbud-type, all the lateral inflorescences are removed and only the terminal inflorescence is allowed to develop.

*Inflorescence bud.*—Height: About 5 mm. Diameter: About 8.5 mm. Shape: Oblate. Color: Close to 146A to more green than 147A.

*Inflorescence diameter.*—Large, about 10.5 cm.

*Inflorescence height.*—About 4.5 cm.

*Diameter of disc.*—About 6.5 mm; inconspicuous.

*Receptacle diameter.*—About 1.5 cm.

*Receptacle height.*—About 1 cm.

*Ray florets.*—Length: About 5.1 cm. Width: About 1.5 cm. Corolla tube length: About 4 mm. Corolla tube diameter: About 1.5 mm. Shape: Elongated oblong. Apex: Acute or emarginate. Base: Attenuate and fused into a corolla tube. Margin: Entire. Orientation: Initially incurved to eventually perpendicular. Texture, upper and lower surfaces: Smooth, glabrous; satiny. Number of ray florets per inflorescence: About 218 arranged in numerous whorls. Color: When opening and fully opened, upper surface: Close to 155D; towards the apex, overlain with close to 71A to 77A; color is more faintly overlain with close to 71A to 77A with development. When opening and fully opened, lower surface: Close to 155D; towards the apex, underlain with close to 71A to 77A; color is more faintly underlain with close to 71A to 77A with development.

*Disc florets.*—Arrangement: Massed at center of receptacle. Length: About 8 mm. Diameter, apex: About 2 mm. Diameter, base: About 2 mm. Shape: Tubular; elongated. Apex: Five-pointed. Number of disc florets per inflorescence: About 22. Color: Immature: Close to 144A. Mature, apex: Close to 9A. Mature, mid-section: Close to 144B. Mature, base: Close to 155D.

*Phyllaries.*—Quantity per inflorescence: About 24 arranged in two to three whorls. Length: About 1.2 cm. Width: About 5 mm. Shape: Lanceolate. Apex: Acute. Base: Truncate. Margin: Entire. Texture, upper surface: Waxy, smooth. Texture, lower surface: Pubescent. Color, upper surface: Close to 146A. Color, lower surface: Close to 146A to more green than 147A.

*Reproductive organs.*—Androecium: Present on disc florets only. Anther length: About 2.5 mm. Anther color: Close to 12A. Pollen amount: None observed. Gynoecium: Present on both ray and disc florets. Style length: About 7.5 mm. Style color: Close to 154D. Stigma color: Close to 9A.

*Seed/fruit.*—Seed and fruit production has not been observed.

Disease/pest resistance: Plants of the new *Chrysanthemum* exhibited good resistance to *Fusarium oxysporum* and *Fusarium solani* in inoculated trials in 2005. Resistance to pests and other pathogens common to *Chrysanthemums* has not been observed on plants grown under commercial greenhouse conditions.

It is claimed:

1. A new and distinct cultivar of *Chrysanthemum* plant named 'Yoorchard Lake', as illustrated and described.

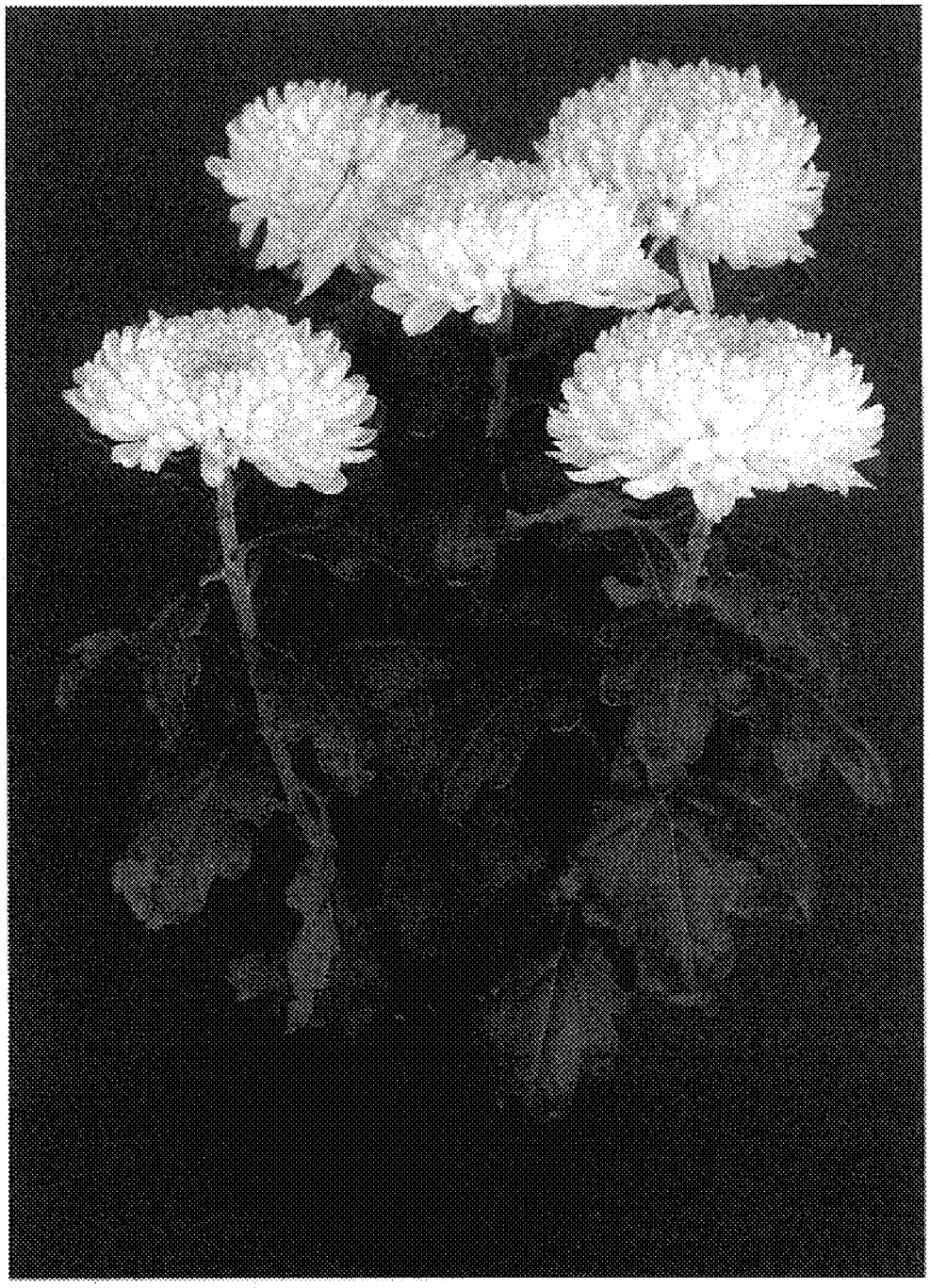

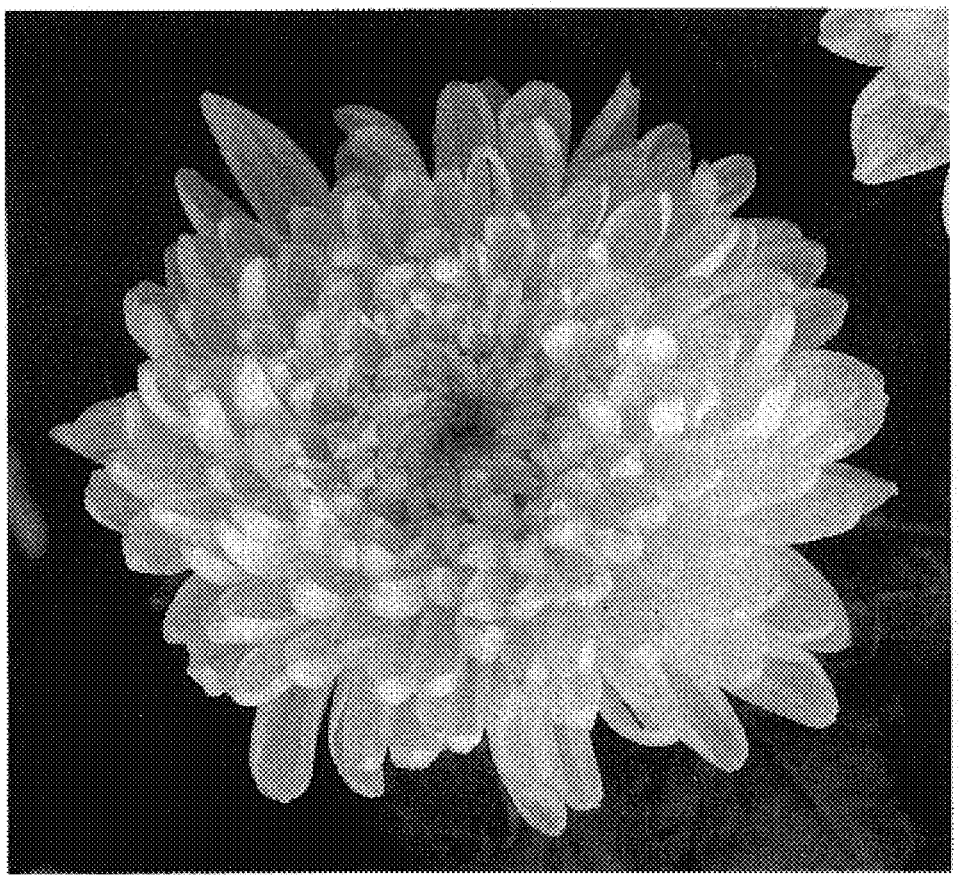

* * * * *